(12) United States Patent
Lin

(10) Patent No.: US 10,981,809 B2
(45) Date of Patent: Apr. 20, 2021

(54) GAS GENERATING APPARATUS WITH SEPARATED WATER PUMP

(71) Applicant: Hsin-Yung Lin, Shanghai (CN)

(72) Inventor: Hsin-Yung Lin, Shanghai (CN)

( * ) Notice: Subject to any disclaimer, the term of this patent is extended or adjusted under 35 U.S.C. 154(b) by 191 days.

(21) Appl. No.: 16/054,652

(22) Filed: Aug. 3, 2018

(65) Prior Publication Data

US 2019/0039921 A1 Feb. 7, 2019

(30) Foreign Application Priority Data

Aug. 4, 2017 (CN) .......................... 201710660677.1

(51) Int. Cl.
*C02F 1/461* (2006.01)
*A61M 16/10* (2006.01)
(Continued)

(52) U.S. Cl.
CPC .......... *C02F 1/4618* (2013.01); *A61M 16/10* (2013.01); *A61M 16/101* (2014.02); *C25B 1/04* (2013.01);
(Continued)

(58) Field of Classification Search
CPC ..... C25B 1/02–12; C25B 15/02; C25B 15/08; C25B 9/13–9/15; C25B 9/17;
(Continued)

(56) References Cited

U.S. PATENT DOCUMENTS

| 3,429,137 A | 2/1969 | Law |
| 5,096,390 A | 3/1992 | Sevrain et al. |

(Continued)

FOREIGN PATENT DOCUMENTS

| CN | 101748420 A | 6/2010 |
| CN | 103451671 A | 12/2013 |

(Continued)

OTHER PUBLICATIONS

Search Report dated Dec. 6, 2018 for European Application No. 18187498.3.

(Continued)

*Primary Examiner* — Alexander W Keeling

(57) ABSTRACT

A gas generating apparatus with separated water pump, comprising a delivery device, an electrolytic device and a water pump. The delivery device accommodates electrolyzed water. The electrolytic device is configured for electrolyzing electrolyzed water to generate hydrogen. The water pump comprises a stirring fan and a drive motor. The stirring fan is configured inside the delivery device to promote the electrolyzed water flowing. The drive motor is coupled to an outer surface of the delivery device and is configured for driving the stirring fan to promote the electrolyzed water flowing. In present invention, the flowing electrolyzed water driven by the separated water pump cools down the electrolytic device, and the drive motor is prevented from corroding by the electrolyzed water and the cooling efficiency of the drive motor is increased. Therefore, the operational safety is improved and the life of the gas generating apparatus with separated water pump is extended.

19 Claims, 13 Drawing Sheets

(51) Int. Cl.
*F04D 13/08* (2006.01)
*C25B 1/04* (2021.01)
*F04D 1/00* (2006.01)
*C25B 15/02* (2021.01)
*C25B 15/08* (2006.01)
*F04D 13/02* (2006.01)
*C02F 103/02* (2006.01)

(52) U.S. Cl.
CPC ............ *F04D 13/024* (2013.01); *F04D 13/08* (2013.01); *A61M 2202/0208* (2013.01); *C02F 2103/026* (2013.01); *C25B 15/02* (2013.01); *C25B 15/08* (2013.01); *F04D 1/00* (2013.01)

(58) Field of Classification Search
CPC ....... C25B 9/00; F04D 13/024; F04D 13/025; F04D 13/026; F04D 13/027; F04D 13/08; F04D 1/00; C02F 1/4618; C02F 2103/026; A61M 16/101; A61M 16/10; A61M 2202/0208
See application file for complete search history.

(56) References Cited

U.S. PATENT DOCUMENTS

| | | | |
|---|---|---|---|
| 2003/0141200 A1 | 7/2003 | Harada | |
| 2004/0112739 A1 | 6/2004 | Kim | |
| 2008/0302670 A1* | 12/2008 | Boyle | ................. C01B 13/0207 205/465 |
| 2009/0038937 A1 | 2/2009 | Conrad | |
| 2011/0293450 A1 | 12/2011 | Grimes et al. | |
| 2012/0045352 A1* | 2/2012 | Lawyer | ................. F04D 29/445 417/410.1 |
| 2014/0010672 A1* | 1/2014 | Naidyhorski | ......... F04D 29/041 417/53 |
| 2014/0138057 A1* | 5/2014 | Horng | ................... F28D 15/046 165/104.26 |
| 2015/0144483 A1* | 5/2015 | Lin | ........................... C25B 9/17 204/274 |
| 2018/0051937 A1* | 2/2018 | Thiers | ...................... F28F 1/10 |

FOREIGN PATENT DOCUMENTS

| | | |
|---|---|---|
| CN | 203618276 | 5/2014 |
| CN | 105624723 A | 6/2016 |
| CN | 105624724 A | 6/2016 |
| CN | 106435633 A | 2/2017 |
| JP | 59-150659 A | 8/1984 |
| JP | 10-179730 A | 7/1998 |
| JP | 11-217680 A | 8/1999 |
| JP | 2003221690 A | 8/2003 |
| JP | 2015127515 A | 7/2015 |
| JP | 2016220505 A | 12/2016 |
| TW | 200303373 | 9/2003 |
| TW | 201615896 | 5/2016 |
| TW | 201712289 | 4/2017 |

OTHER PUBLICATIONS

Notification of Reason for Refusal dated Oct. 6, 2020 for related Japanese Patent Application No. 2018-146993.

* cited by examiner

GAS GENERATING APPARATUS WITH SEPARATED WATER PUMP

CROSS-REFERENCE TO RELATED APPLICATIONS

This application claims the priority benefit of Chinese Application Serial No. 201710660677.1 filed Aug. 4, 2017 the disclosure of which is incorporated herein by reference.

FIELD OF THE INVENTION

The present invention relates to a gas generating apparatus, more particularly, to a gas generating apparatus having a separated water pump to promote the electrolyzed water flowing.

DESCRIPTION OF THE PRIOR

As people have always been paying much attention on health developments, many developments in medical technology are often targeted on treating diseases and prolonging human lifetime. Most of the treatments in the past are passive, which means that the disease is treated only when it occurs, and the treatments may include an operation, a medication treatment, a radiation therapy, or a medical treatment for cancer. However, in recent years, most of the medical experts' researches are gradually moving towards preventive medical methods, such as research on healthy food, screening and the prevention of inherited diseases, which actively prevents diseases from occurring in the future. Due to the focus of the prolongation of human life, many anti-aging and anti-oxidation technologies including skin care products and anti-oxidation food/medicine are gradually being developed and are becoming increasingly popular to the general public.

Studies have found that there are instable oxygen species (O+), also known as free radicals, in the human body. The free radicals which are usually generated due to diseases, diet, environment and one's lifestyle can be excreted in the form of water by reacting with the inhaled hydrogen. With this method, the amount of free radicals in the human body can be reduced, thereby restoring the body condition from an acidic state to an alkaline state, achieving an anti-oxidation, anti-aging and beauty health effect, and even eliminating chronic diseases. Furthermore, there are also clinical experiments showing that patients who need to inhale a high concentration of oxygen for an extended period of time would experience lung damage, but they could be ameliorated by inhaling hydrogen.

The general electrolytic device generates hydrogen by using electrolyzed water for inhaling. The temperature of electrolytic device is increasing due to continuous operation. In order to avoid the excessive heat of the electrolytic device internal units contribute to the operational risk, the liquid water in the electrolytic device is often used to assist the electrolysis device to dissipate heat. The heat of the electrolytic device is taken away since a stirring device promotes the liquid water flowing. However, the corrosion characteristic of the electrolytes in the electrolyzed water rapidly decreases the use period of the stirring device.

SUMMARY OF THE INVENTION

In view of this, the present invention provides a gas generating apparatus with separated water pump for electrolyzing water to generate hydrogen. At the meanwhile, a separated water pump is configured for promoting the water flowing to assist the electrolysis device heat dissipation, and the cooling efficiency is increased by using a cooling tube with a copper powder sintered outer surface. The present invention configures a drive motor outside the electrolyzed water to promote the water flowing, so that the drive motor is prevented from the corrosion of the electrolyzed water. Moreover, the cooling efficiency of the drive motor is increased and the control units are reduced. Therefore, the gas generating apparatus with separated water pump operational safety is improved and the use period of the gas generating apparatus with separated water pump is extended.

An object of the present invention is to provide a gas generating apparatus with separated water pump comprising a delivery device, an electrolytic device, and a water pump. The delivery device accommodates electrolyzed water. The electrolytic device is coupled to the delivery device and is configured for generating hydrogen. The water pump comprises a stirring fan and a drive motor. The stirring fan is accommodated in the delivery device to promote the electrolyzed water flowing. The drive motor is coupled to the outer surface of the delivery device and is configured for driving the stirring fan to promote the electrolyzed water flowing. Wherein, the drive motor is non-mechanically connected to the stirring fan.

In another embodiment, the gas generating apparatus with separated water pump further comprises a cooling device coupled to the delivery device. The cooling device is configured for dissipating the heat of the electrolyzed water. The stirring fan promotes the electrolyzed water flowing through the cooling device.

According to another embodiment of the present invention, the cooling device further comprises a cooling tube, and a surface of the cooling tube has a copper powder sintered layer.

In another embodiment, the gas generating apparatus with separated water pump further comprises a heat pipe. An endothermic end of the heat pipe is configured on the cooling device.

Furthermore, according to another embodiment, the endothermic end of the heat pipe has a flat structure; the flat structure has a recession, and the cooling device is coupled to the recession.

According to another embodiment, the delivery device has a hole, and the water pump further comprises a seal ring. The drive motor is coupled to the hole by the seal ring.

In another embodiment, the drive motor drives the stirring fan by magnetic coupling.

According to another embodiment, the stirring fan is suspended in the electrolyzed water.

In another embodiment, the gas generating apparatus with separated water pump further comprises a connecting component. The stirring fan is coupled to the delivery device by the connecting component.

According to another embodiment, a shell of the drive motor has no control circuit board inside, and the gas generating apparatus with separated water pump further comprises a control circuit board configured outside the shell and electrically connected to the drive motor. The control circuit board is configured for controlling the drive motor to drive the stirring fan.

Another object of the present invention is to provide a gas generating apparatus with separated water pump comprising a delivery device, an electrolytic device, a cooling device, and a water pump. The delivery device accommodates electrolyzed water. The electrolytic device is coupled to the delivery device and is configured for generating hydrogen. The cooling device is coupled to the delivery device and is for dissipating the heat of the electrolyzed water. The water pump comprises a stirring fan and a drive motor. The stirring fan is accommodated in the delivery device to promote the electrolyzed water flowing. The drive motor is coupled to the outer surface of the delivery device and is configured for driving the stirring fan to promote the electrolyzed water flowing. Wherein, the drive motor is non-mechanically connected to the stirring fan.

In another embodiment, the drive motor has a shell, and the shell has no control circuit board inside, and the gas generating apparatus with separated water pump further comprises a control circuit board configured outside the shell and electrically connected to the drive motor. The control circuit board is configured for controlling the drive motor to drive the stirring fan.

According to another embodiment of the present invention, the cooling device further comprises a cooling tube, and a surface of the cooling tube has a copper powder sintered layer.

In another embodiment, the gas generating apparatus with separated water pump further comprises a heat pipe. An endothermic end of the heat pipe is configured on the cooling device.

Furthermore, according to another embodiment, the endothermic end of the heat pipe has a flat structure; the flat structure has a recession, and the cooling device is coupled to the recession.

In another embodiment, the endothermic end of the heat pipe is formed by partial housing of the cooling device.

According to another embodiment, the water pump further comprises a fixing component for fixing the drive motor on the outer surface of the delivery device.

In another embodiment, the drive motor is a DC brushless motor.

In another embodiment, the drive motor drives the stirring fan by magnetic coupling.

According to another embodiment, the stirring fan is suspended in the electrolyzed water.

In summary, the main point of the present invention is to provide a gas generating apparatus with separated water pump comprising the electrolytic device and the water pump. In the gas generating apparatus with separated water pump of the present invention, the electrolytic device is configured for generating hydrogen to provide human to inhale. The drive motor outside the electrolyzed water in the water pump drives the stirring fan in the electrolyzed water in non-mechanically connected way to promote the electrolyzed water flowing through the cooling device. Therefore, the drive motor is prevented from electrolyzed water corrosion while the water pump assists the electrolysis device to dissipate heat. Moreover, the cooling efficiency of the drive motor is increased and the control units are reduced. Since the cooling device comprises a cooling tube with a surface having a copper powder sintered layer, the heat exchange efficiency of the cooling device is increased and the working temperature of the gas generating apparatus is reduced. Therefore, the gas generating apparatus with separated water pump operational safety is improved and the use period of the gas generating apparatus with separated water pump is extended.

BRIEF DESCRIPTION OF THE APPENDED DRAWINGS

Some of the embodiments will be described in detail, with reference to the following figures, wherein like designations denote like members, wherein.

The advantages, spirits, and features of the present invention will be explained and discussed with embodiments and figures as follows

DETAILED DESCRIPTION OF THE INVENTION

A detailed description of the hereinafter described embodiments of the disclosed apparatus and method are presented herein by way of exemplification and not limitation with reference to the Figures. Although certain embodiments are shown and described in detail, it should be understood that various changes and modifications can be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

Figure 1:
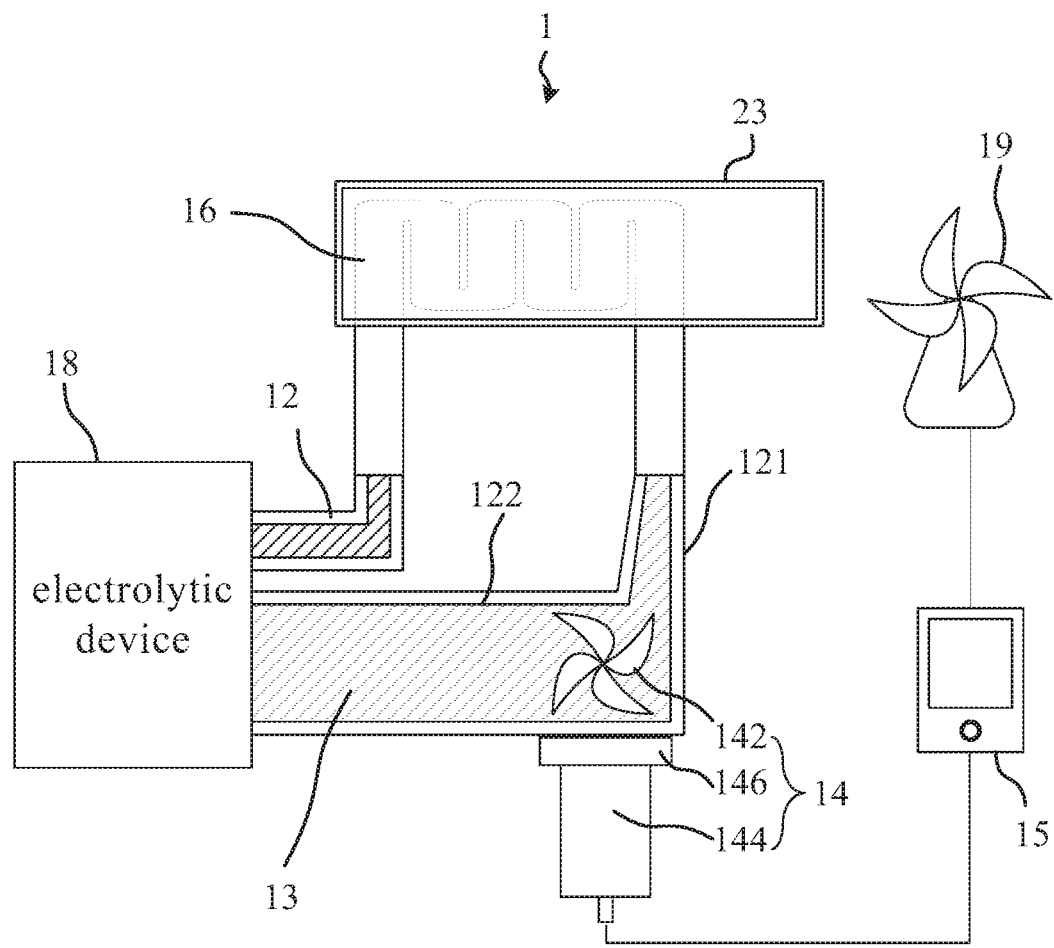
FIG. 1 illustrates a schematic diagram of an embodiment of the gas generating apparatus with separated water pump of the present invention.

Please refer to FIG. 1. FIG. 1 illustrates a schematic diagram of an embodiment of the gas generating apparatus with separated water pump 1 of the present invention. According to an embodiment of the present invention, the present invention provides a gas generating apparatus with separated water pump 1 comprising a delivery device 12, an electrolytic device 18, and a water pump 14. The delivery device 12 accommodates electrolyzed water 13 and has an outer surface 121. The electrolytic device 18 is coupled to the delivery device 12 and is configured for electrolyzing the electrolyzed water 13 to generate hydrogen. The water pump 14 comprises a stirring fan 142 and a drive motor 144. The stirring fan 142 is accommodated in the delivery device 12 to promote the electrolyzed water 13 flowing. The drive motor 144 is coupled to the outer surface 121 of the delivery device 12 and is configured for driving the stirring fan 142 to promote the electrolyzed water 13 flowing. Wherein, the drive motor 144 is non-mechanically connected to the stirring fan 142.

In practice, the electrolytic device 18 may be a two-electrode type electrolytic cell. When the electrolytic cell is energized, the two electrodes of the cell can simultaneously electrolyze the water to produce hydrogen and oxygen. If the generated gas is accommodated in the same space, the mixed gas of hydrogen and oxygen can be generated. The ratio of hydrogen to oxygen in the mixed gas of hydrogen and oxygen is about 2:1. In another practice, the electrolytic device 18 may be an ion membrane electrolytic device. The ion exchange membrane is set between an anode chamber and a cathode chamber, wherein oxygen is generated by an anode electrode in the anode chamber and hydrogen is generated by a cathode electrode in the cathode chamber. Besides, the ion membrane electrolytic device can further comprise a gas flow meter connected to the anode chamber and the cathode chamber respectively, so that the concentration ratio of hydrogen and oxygen is regulated as-needed and the mixed gas of hydrogen and oxygen is outputted. In an embodiment, the mixed gas of hydrogen and oxygen can be pure hydrogen, pure oxygen, or any proportion of the hydrogen and oxygen for human to heal. Furthermore, external gas can be accessed. The generated hydrogen, oxygen or the mixed gas of hydrogen and oxygen is mixed with the external gas to a concentration ratio as-needed for different subsequent applications. Wherein, the external gas may be air, water vapor, volatile gas or noble gas.

The electrolytic device 18 generates the hydrogen by consumption of liquid water in the electrolyzed water 13, and the electrolyte in the electrolyzed water 13 is configured for assisting in electrolyzing and generating hydrogen. Therefore, the liquid water is consumed and the electrolyte is preserved while the electrolytic device 18 is electrolyzing. Since the consumption of liquid water is out of proportion to the electrolyte, the electrolyte concentration in the electrolyzed water 13 around the electrode plate turns to change the electrolysis efficiency while electrolyzing. On the other hand, the surface of the electrode plate generates hydrogen and oxygen while electrolyzing. If the gas is not removed from the electrode plate immediately and attaches to the electrode plate surface, the surface area of the electrode plate for contacting the electrolyzed water 13 to electrolyze will be lower when the gas is not attached, which means that the electrolyzing efficiency of the electrode plate will be reduced. In summary, the mentioned electrolyzing way results in poor electrolyzing efficiency; at the same time, the electrode plate could not contact the electrolyzed water effectively and then cause the risk of air burning. Therefore, the flowing electrolyzed water 13 is necessary to reduce the concentration-changing rate of the electrolyte; at the meanwhile, the flowing electrolyzed water 13 is used to take bubbles away from the electrode plate, so that to make sure that the surface of the electrode plate is enough for the contact of the electrolyzed water 13. At the same time, in order to avoid the excessive heat accumulation of the electrolytic device 18 during operation, the heat of the electrolytic device 18 can be taken away from the heat source of the electrolytic device 18 by the flowing electrolyzed water 13. Therefore, the electrolytic device 18 dissipates heat much quickly.

The stirring fan 142 is accommodated in the delivery device 12 since the stirring fan 142 is to promote the electrolyzed water 13 flowing. The drive motor 144 in the gas generating apparatus with separated water pump 1 is coupled to the stirring fan 142 to drive the stirring fan 142 to work for promoting the electrolyzed water 13 flowing. In an embodiment, the stirring fan 142 is accommodated in the electrolyzed water 13. In another embodiment, the delivery device 12 may not be filled with the electrolyzed water 13, and the stirring fan 142 is accommodated in the delivery device 12 but located outside the electrolyzed water 13. Wherein, the stirring fan 142 can move in the way of peristalsis, swinging, vibrating or rotating to promote the electrolyzed water 13 flowing. In an embodiment, the gas generating apparatus with separated water pump 1 promotes the electrolyzed water 13 flowing by the rotating of the stirring fan 142. The gas generating apparatus with separated water pump 1 that promotes the electrolyzed water 13 flowing may be in a way that the electrolyzed water 13 is sucked into the stirring fan 142 in axial direction, and then the electrolyzed water 13 is exported from the side direction of the stirring fan 142. It also means the water pump 14 can be a type of the radial pump (centrifugal pump). However, the type of the water pump 14 is not limited to the radial pump. The water pump 14 can also be a type of axial pump, mixed pump combined radial and axial pump, or any type which could promote the electrolyzed water 13 flowing.

Figure 2:
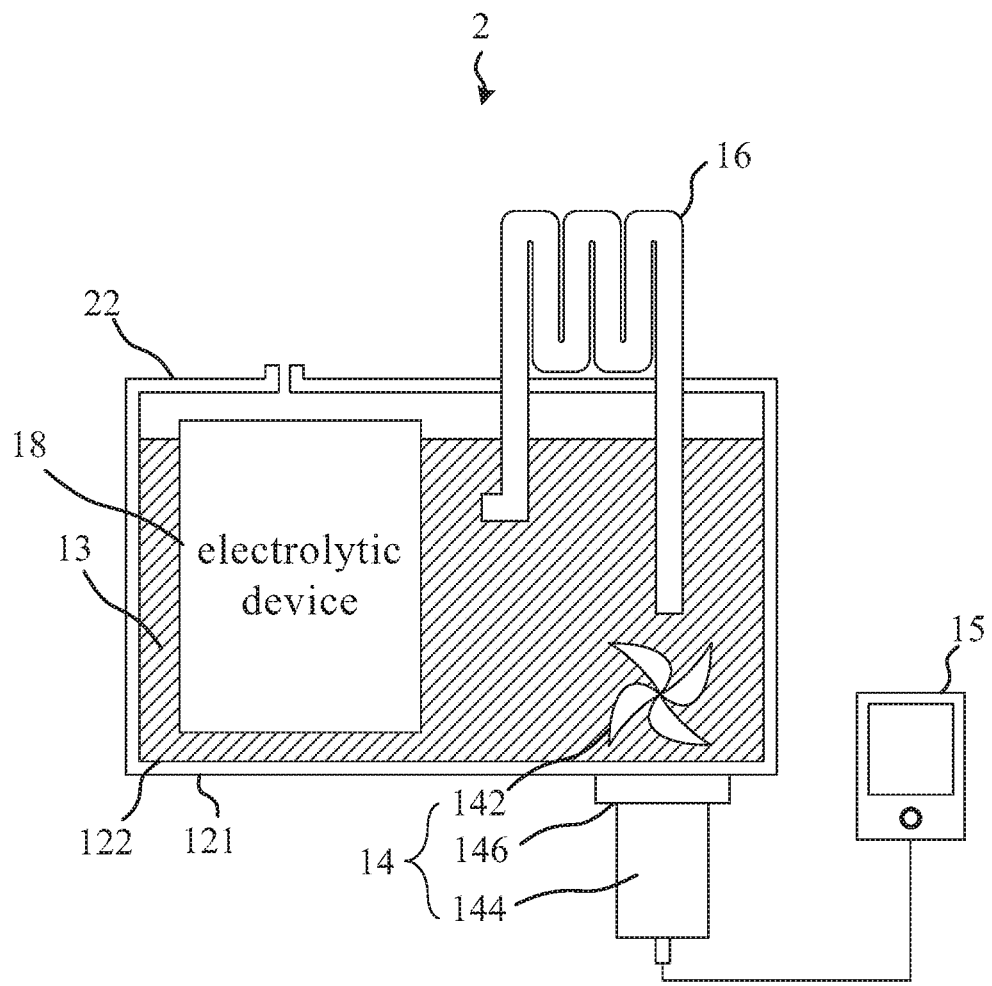
FIG. 2 illustrates a schematic diagram of another embodiment of the gas generating apparatus with separated water pump of the present invention.

Please refer to FIG. 2. FIG. 2 illustrates a schematic diagram of another embodiment of the gas generating apparatus with separated water pump 1 of the present invention. Since the electrolytic device 18 generates the hydrogen by electrolyzing the liquid water, the electrolytic device 18 is need to be configured at a position the electrolyzed water 13 can be received. In an embodiment, the electrolytic device 18 is just configured in the delivery device 22 to receive the electrolyzed water 13 to generate the hydrogen. Therefore, the delivery device 22 can accommodate the electrolytic device 18 as shown in FIG. 2, or the delivery device 22 and the electrolytic device 18 can be connect to each other as shown in FIG. 1.

The electrolyzed water 13 may contain the electrolyte prone to corrode the component. If the drive motor 144 for driving the stirring fan 142 is also accommodated in the electrolyzed water 13, the components of the drive motor 144 are likely to be damaged and the use period of the drive motor 144 is decreased. Therefore, the present invention configures the drive motor 144 out of the electrolyzed water 13 to reduce the damage probability of the drive motor 144. Besides, since the drive motor 144 is coupled to the outer surface 121 of the delivery device 12, the volume of the drive motor 144 is not limited to the accommodating space in the delivery device 12; it also means that the geometric appearance limit of the drive motor 144 is reduced. In addition, the drive motor 144 generates heat while working. The heat of the drive motor 144 enhances the corrosion speed of the electrolyzed water 13 when the drive motor 144 is configured in the electrolyzed water 13; moreover, the working loading of the electrolyzed water 13 is exacerbated because the electrolyzed water 13 also cools down the electrolytic device 18. Therefore, the mentioned problem can be solved when the drive motor 144 is coupled to the outer surface 121 of the delivery device 12. Besides, since the volume of the drive motor 144 is not limited, the cooling component can be enlarged to enhance the heat dissipation. Furthermore, the drive motor 144 is configured outside the electrolyzed water 13 to avoid the corrosion of the circuit components by electrolytes, and the circuit components can be integrated in the electronic control system of the gas generating apparatus with separated water pump 2 to reduce the equipment requirements. It means the shell of the drive motor 144 has no control circuit board inside, but another control circuit board 15 controls the drive motor 144 to drive the stirring fan 142. The control circuit board 15 is configured outside the shell of the drive motor 144 and electrically connected to the drive motor 144. The separating configured way can prevent the heat source of the control circuit board 15 from adversely affecting the drive motor 144. Furthermore, the drive motor 144 in working will not be prone to electromagnetic interfere with the electrolytic device 18 performing the electrolyzation.

Figure 3:
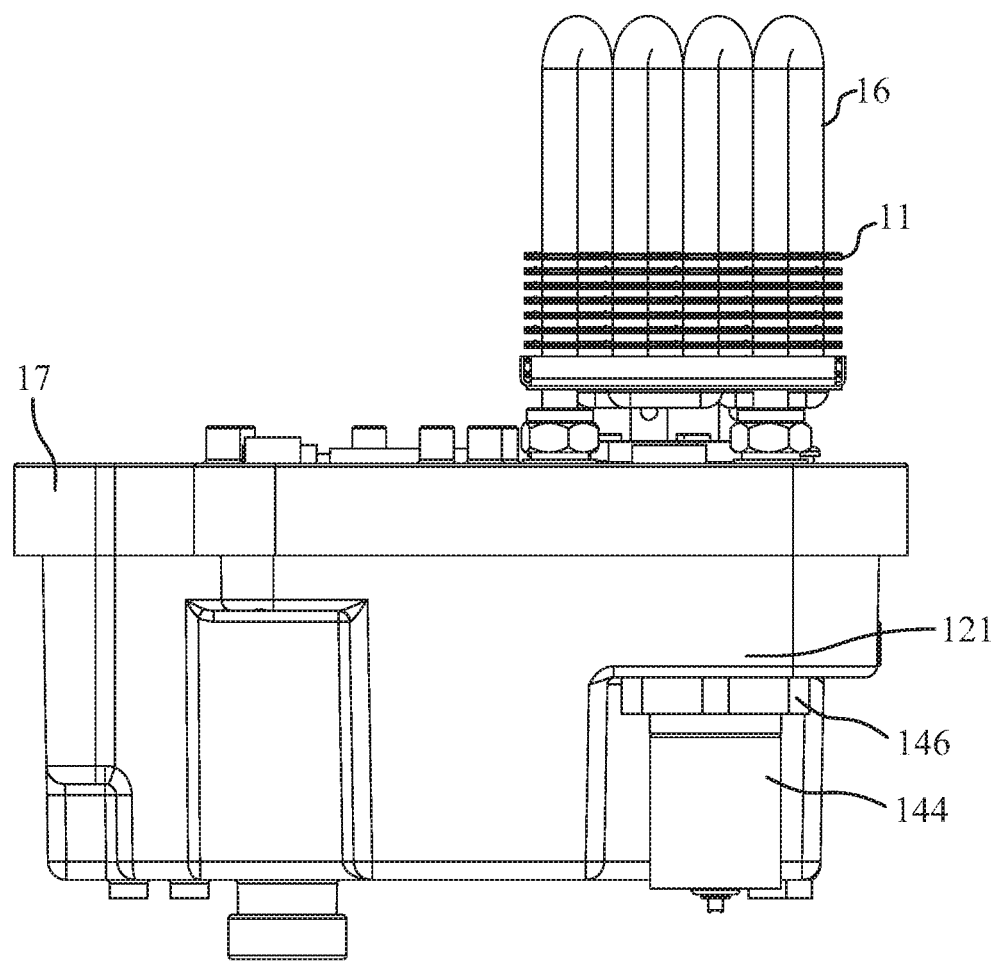
FIG. 3 illustrates a schematic diagram of an embodiment according to FIG. 1.
Figure 4:
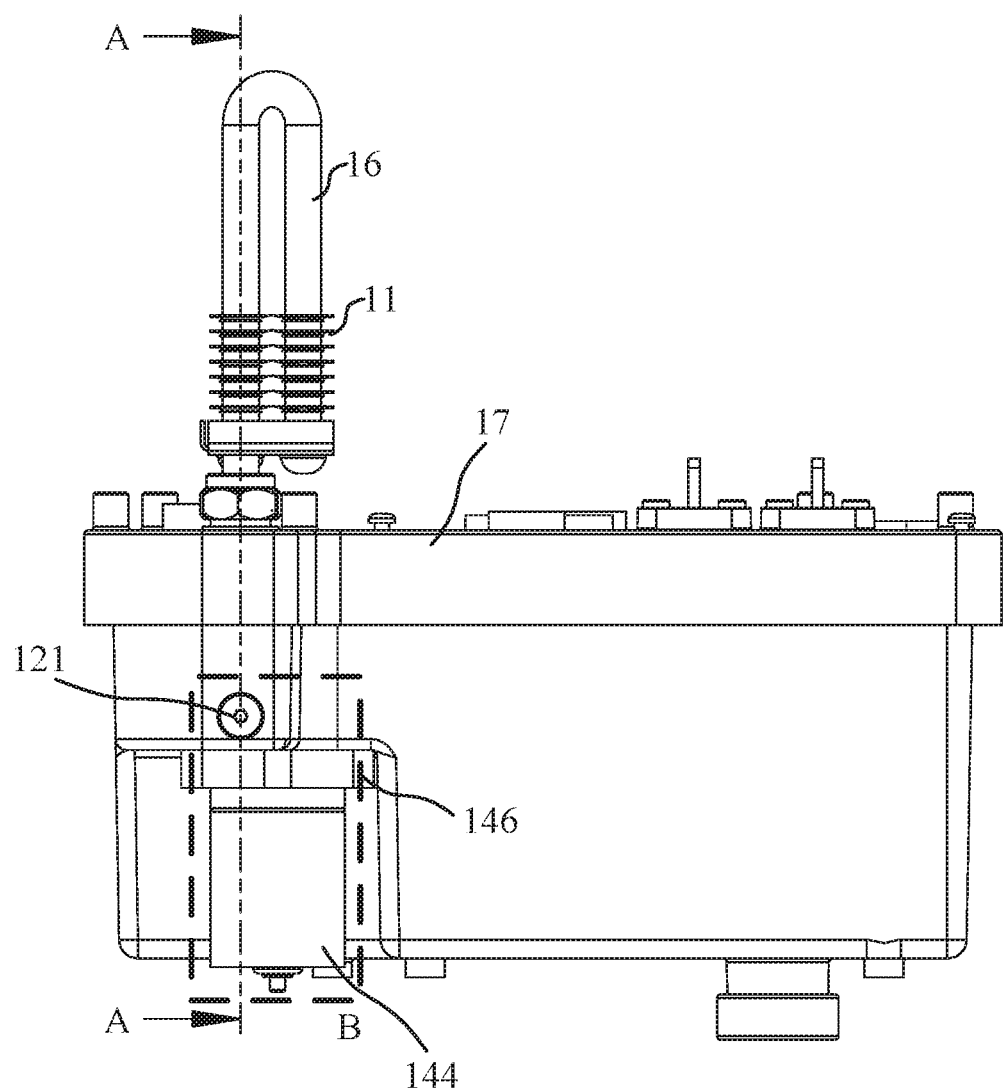
FIG. 4 illustrates a schematic diagram of another perspective of FIG. 3.
Figure 5:
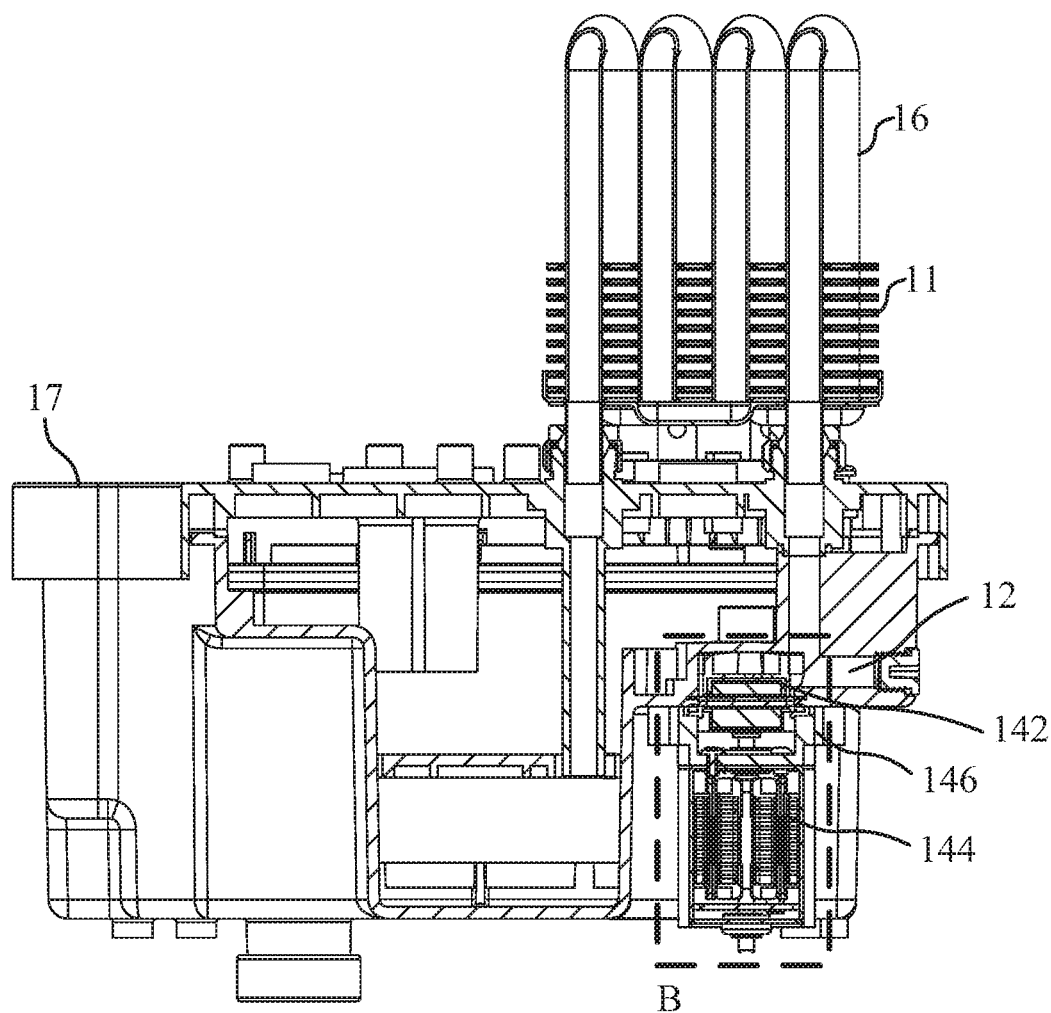
FIG. 5 illustrates a sectional view taken along line A-A of FIG. 4.
Figure 6:
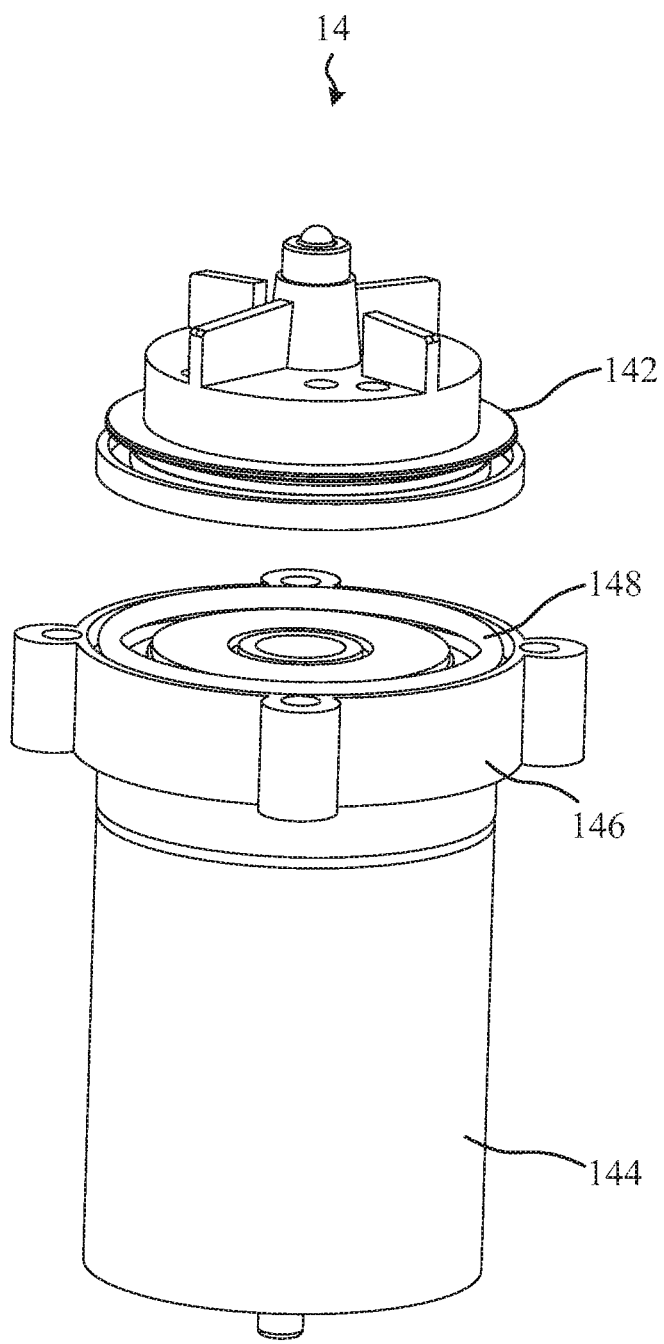
FIG. 6 illustrates a schematic diagram of an embodiment of a water pump.
Figure 7:
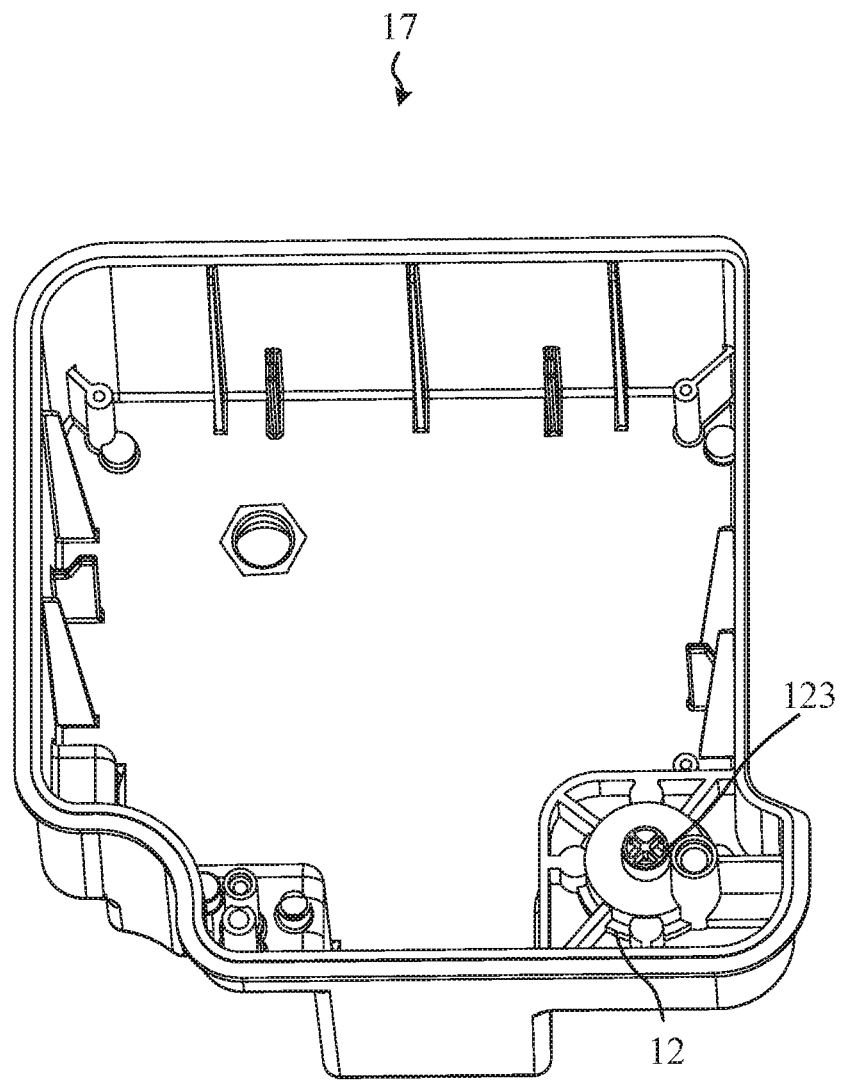
FIG. 7 and FIG. 8 illustrate schematic diagrams of another perspective of the water tank of FIG. 3.
Figure 8:
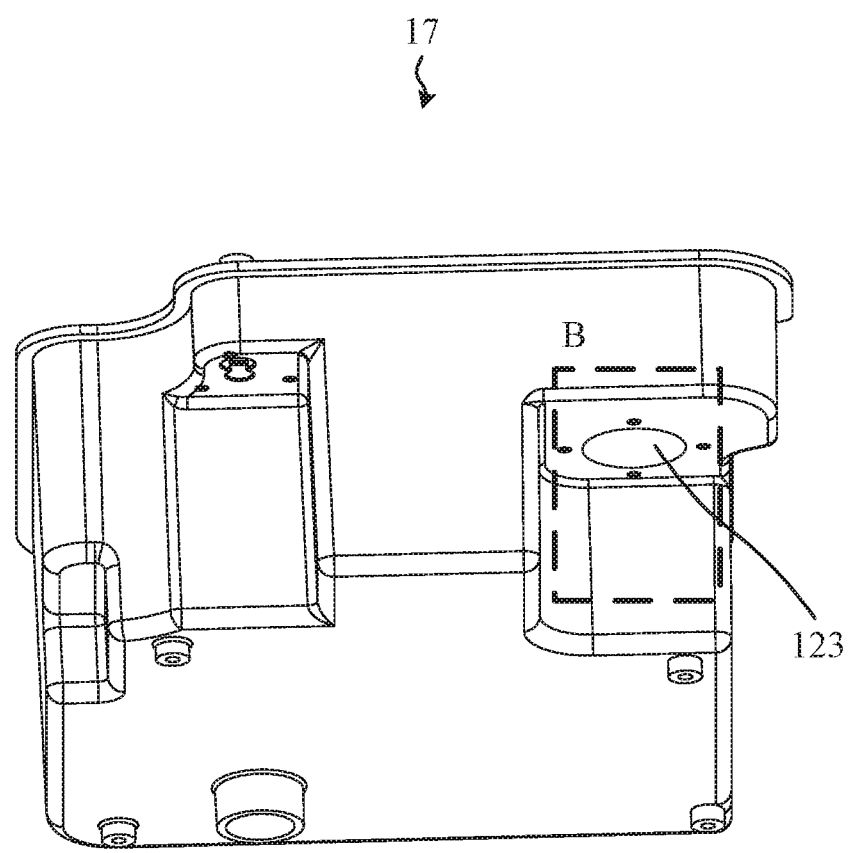
Figure 9:
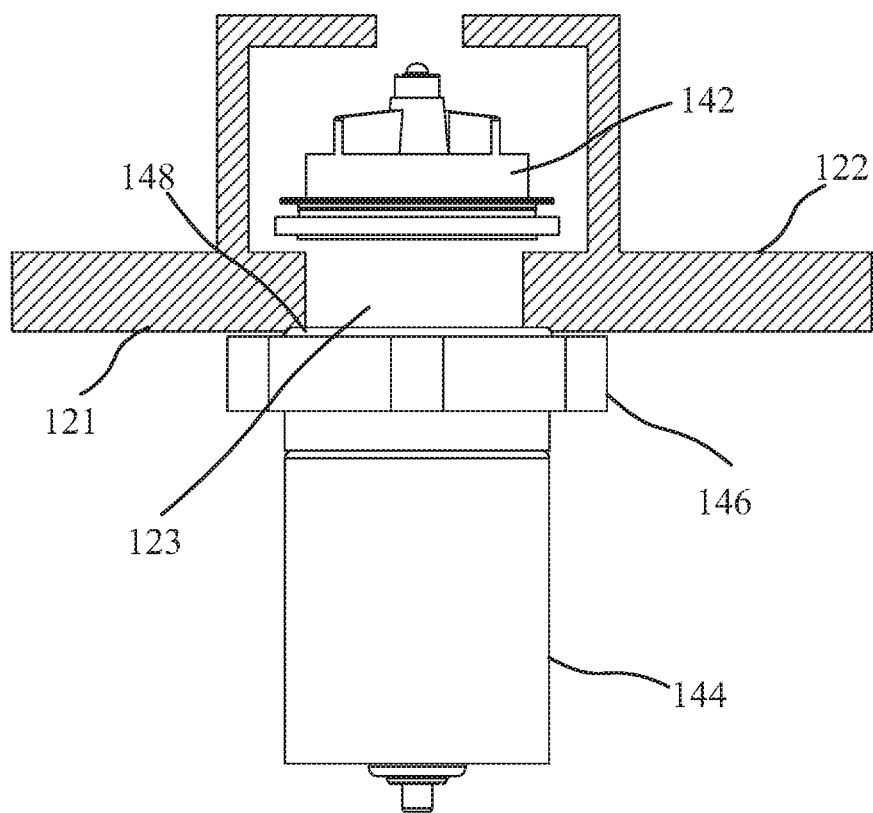
FIG. 9 to FIG. 13 illustrate schematic diagrams of water pump coupled to delivery device in different embodiments of the gas generating apparatus with separated water pump of the present invention.

Please refer to FIG. 1, FIG. 3 to FIG. 8. FIG. 3 illustrates a schematic diagram of an embodiment according to FIG. 1. FIG. 4 illustrates a schematic diagram of another perspective of FIG. 3. FIG. 5 illustrates a sectional view taken along line A-A of FIG. 4. FIG. 6 illustrates a schematic diagram of an embodiment of a water pump 14. FIG. 7 and FIG. 8 illustrate schematic diagrams of another perspective of the water tank 17 of FIG. 3. In an embodiment, the gas generating apparatus with separated water pump further comprises a water tank 17 for accommodating the electrolytic device 18 and the electrolyzed water 13. The delivery device 12 is formed at the water tank 17. The electrolytic device 18 receives the electrolyzed water 13 by the water tank 17, and the stirring fan 142 promotes the electrolyzed water 13 flowing by the loading of the water tank 17. In practice, the gas generating apparatus with separated water pump 1 further comprises a cooling device 16 coupled to the delivery device 12, and the stirring fan 142 promotes the electrolyzed water 13 flowing through the cooling device 16 to be cooled down. Wherein, the electrolyzed water 13 may flow into the cooling device 16 or flow through the surface of the cooling device 16 to dissipate the heat by the cooling device 16. Furthermore, the electrolyzed water 13 accommodated in the delivery device 12 has a liquid level, and the cooling device 16 may have a part higher than the liquid level. The exposed part of the cooling device 16 is cooled down by natural cooling or blown by the cooling fan 19 to assist in decreasing the electrolyzed water 13. In practice, the cooling fan 19 may drive the external air to blow to the cooling device 16 to dissipate the heat of the cooling device 16. In another embodiment, the cooling fan 19 is configured on the shell of the generator 1 and is used to drive the external air to flow into the gas generating apparatus with separated water pump 1 or exhaust the air in the gas generating apparatus with separated water pump 1 outside. The driving air passes through the cooling device 16 via the configured gas pathway due to the pressure difference, so that the heat of the cooling device 16 is taken away. Besides, the cooling fan 19 may be controlled by the mentioned control circuit board 15, so that the electronic control system of the gas generating apparatus with separated water pump 1 can be further integrated.

In practice, part of the cooling device 16 may be located out of the delivery device 12 to further be dissipated by other cooling elements. In practice, the cooling device 16 can have a cooling tube. The cooling tube can be made of metal, and further, the cooling tube may be a stainless steel tube or a copper tube. The high heat conductivity material of the cooling tube makes the gas generating apparatus with separated water pump 1 increases the heat conductivity rate. In another embodiment, the cooling tube can have an inner side with copper powder sintered, so that the area of the cooling tube contacted with the electrolyzed water 13 and the conductivity rate are both increased. In another embodiment, a surface of the cooling tube can have a copper powder sintered layer, so that the heat exchange rate is increased. Furthermore, the gas generating apparatus with separated water pump 1 may comprise one or more cooling sheets 11 configured on the cooling device 16 to assist cooling device 16 cooling down. Besides, the gas generating apparatus with separated water pump 1 may comprise a heat pipe 23 configured in the gas generating apparatus with separated water pump 1 to absorb the heat in the electrolyzed water 13. Wherein, the heat pipe 23 may be accommodated in the electrolyzed water 13 directly or partially, so that the heat of the electrolyzed water 13 is taken away. In an embodiment, the exterior of the heat pipe 23 is a thin film structure, so that the effective area of the endothermal end and the exothermal end are increased. In another embodiment, the endothermal end of the heat pipe 23 has a flat structure, and the flat structure has a recession. The cooling device is coupled to the recession. Furthermore, the endothermal end of the heat pipe 23 has an accommodation, for example, a heat conduction chamber. The cooling device 16 is coupled to the accommodation to enhance the heat exchange rate of the cooling device 16. In another embodiment, the shell of the heat pipe 23 endothermal end is directly formed by partial housing of the cooling device 16. The working fluid in the heat pipe 23 directly absorbs the heat of the cooling device 16 via the endothermal end of the heat pipe 23. In an embodiment, the cooling fan 19 drives the external air to flow to the cooling sheet 11 or the exothermal end of the heat pipe 23 to remove the heat of the cooling device 16. In an embodiment, the cooling sheet 11 or the exothermal end of the heat pipe 23 are directly formed on the shell of the gas generating apparatus with separated water pump 1 or contacted with the shell of the gas generating apparatus with separated water pump 1 to assist heat dissipation by external surrounding.

In an embodiment, the drive motor 144 located at the outer surface 121 drives the stirring fan 142 accommodated in the electrolyzed water 13 by magnetic coupling. Furthermore, the drive motor 144 drives the stirring fan 142 to rotate by magnetic coupling. In practice, the drive motor 144 may be a DC (direct current) motor; moreover, the drive motor 144 may be a DC brushless motor to construct a water pump 14 with low energy consumption and long use period.

Figure 10:
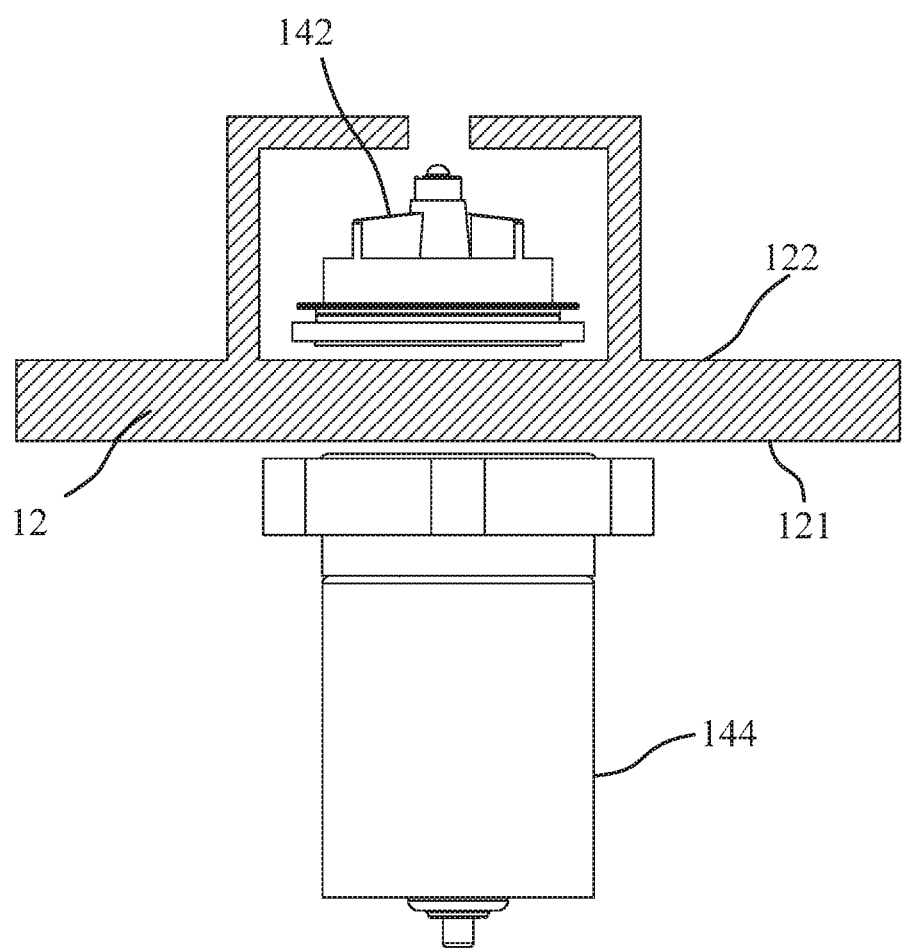
Figure 11:
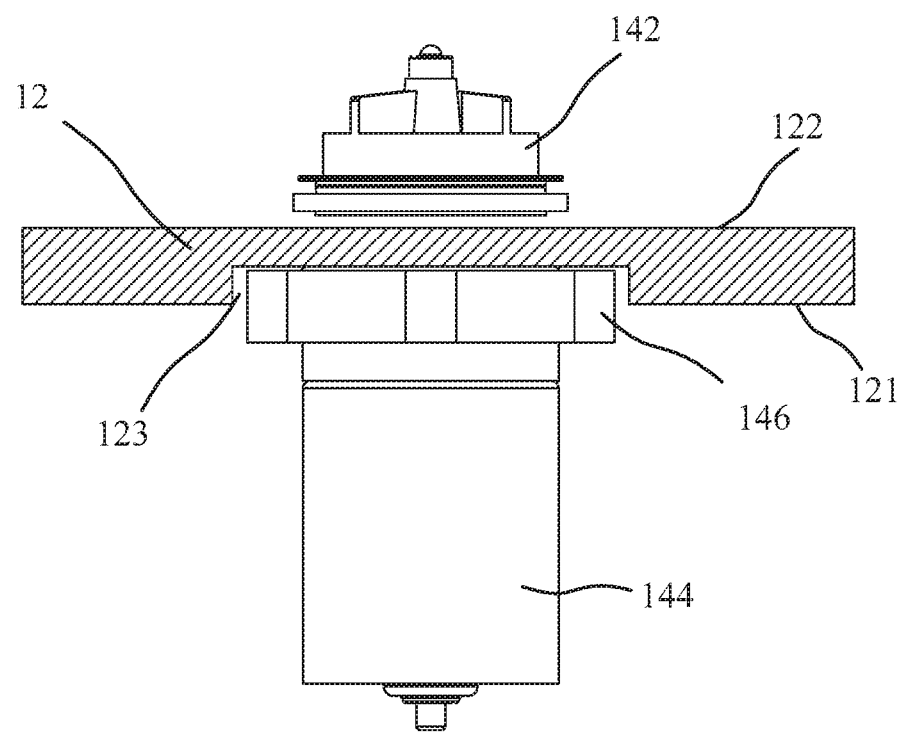
Figure 12:
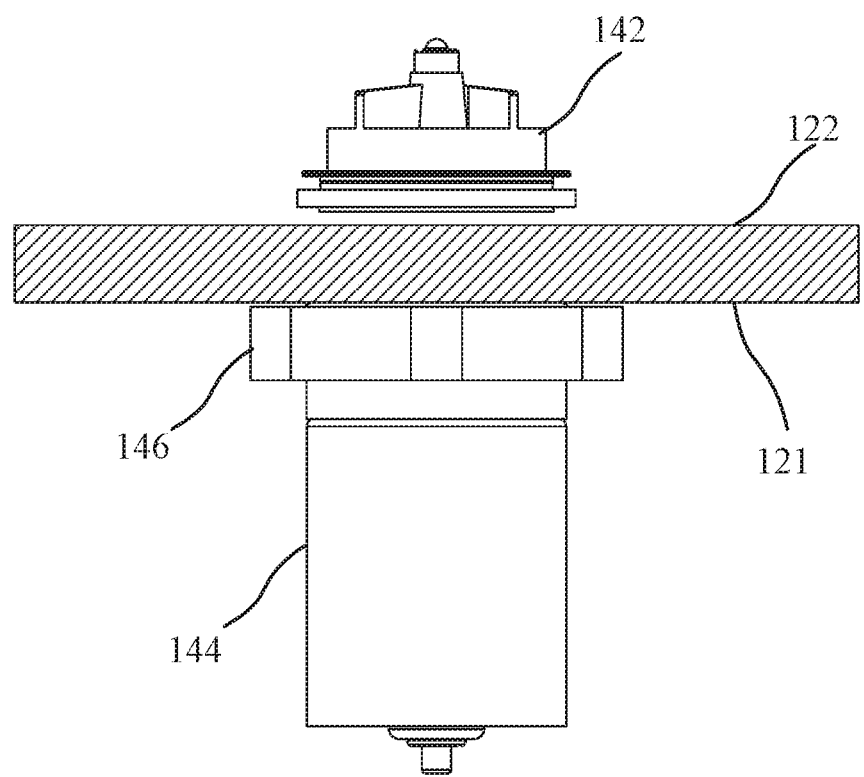
Figure 13:
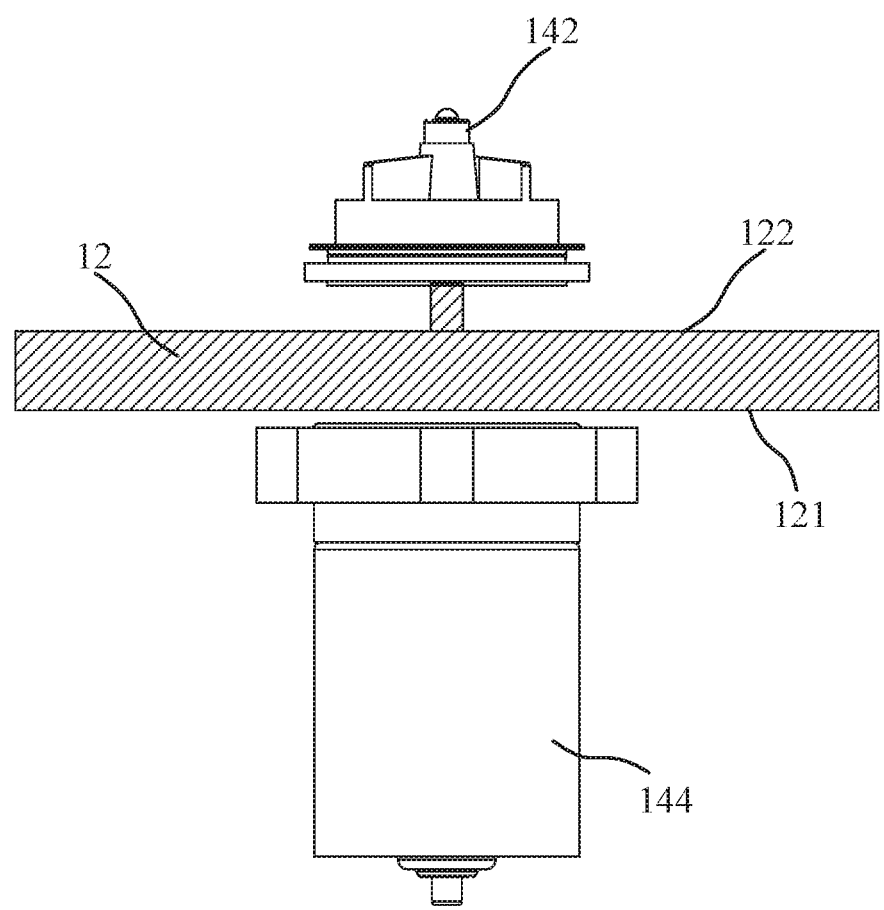

Please refer to FIG. 7 to FIG. 13. FIG. 9 to FIG. 13 illustrate schematic diagrams of water pump 14 coupled to delivery device 12 in different embodiments of the gas generating apparatus with separated water pump 1 of the present invention. In an embodiment, the delivery device 12 has a hole 123, the water pump 14 further comprises a seal ring 148, and the drive motor 144 is coupled to the hole 123 by the seal ring 148 as shown in FIG. 7 to FIG. 13. Furthermore, the drive motor 144 may embed in the hole 123. Besides, the stirring fan 142 is suspended in the electrolyzed water 13, and the stirring fan 142 is magnetically coupled to the drive motor 144. In the present embodiment, the stirring fan 142 is coupled to the delivery device 12 and is accommodated in the mentioned hole 123. The locations of the stirring fan 142 and the drive motor 144 are limited by the locations of the hole 123. In another embodiment, the moving location of the stirring fan 142 is limited by the coupled delivery device 12 as shown in FIG. 10. The drive motor 144 is not configured on the outer surface 121 of the delivery device 12, but the drive motor 144 still can cross the outer surface 121 and drive the stirring fan 142 by magnetic coupling. In another embodiment, the mentioned hole 123 does not pass through the shell of the delivery device 12 as shown in FIG. 11. The water pump 14 further comprises a fixing component 146. The drive motor 144 is embedded on the hole 123 and fixed on the outer surface 121 of the delivery device 12 by the fixing component 146. Besides, the delivery device 12 has an inner surface 122. The stirring fan 142 is coupled to the inner surface 122 corresponding to the drive motor 144 by magnetic coupling. In an embodiment, the drive motor 144 is not embedded on the outer surface 121 but is fixed on the outer surface 121 by the fixing component 146 as shown in FIG. 12. Besides, the mentioned stirring fan 142 can also pin-jointed on the delivery device 12 by a connecting component as shown in FIG. 13.

In practice, the gas generating apparatus with separated water pump 1 may further comprise a gas mixing device. The gas mixing device is configured for mixing the gas generated by the electrolytic device 18 with a specific gas to form a healthy gas for further using. Wherein, the specific gas is selected from one of the groups consisting of water vapor, atomized solution, volatile essential oil and combinations thereof. Besides, the gas mixing device can be imported with the specific gas to combine with the gas generated by the electrolytic device 18 to form a healthy gas; otherwise, the precursor of the specific gas, such as essential oils, syrups, pure water, or the combinations thereof, can be shacked and atomized to form the specific gas, and then the specific gas combines with the gas generated by the electrolytic device 18 to form a healthy gas.

In summary, in the gas generating apparatus with separated water pump of the present invention, the electrolytic device is configured for generating hydrogen to provide human to inhale. The drive motor outside the electrolyzed water in the water pump drives the stirring fan in the electrolyzed water in non-mechanically connected way to promote the electrolyzed water flowing through the cooling device. Therefore, the drive motor is prevented from electrolyzed water corrosion while the water pump assists the electrolysis device to dissipate heat. Moreover, the cooling efficiency of the drive motor is increased and the control units are reduced. Since the cooling device comprises a cooling tube with a surface having a copper powder sintered layer, the heat exchange efficiency of the cooling device is increased and the working temperature of the gas generating apparatus with separated water pump is reduced. Therefore, the gas generating apparatus with separated water pump operational safety is improved and the use period of the gas generating apparatus with separated water pump is extended.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A gas generating apparatus, comprising:
   a water tank comprising a casing and forming an accommodating space for accommodating an electrolyzed water;
   an electrolytic device disposed in the accommodating space of the water tank and configured for generating a hydrogen;
   a cooling device comprising at least one cooling tube and a plurality of cooling sheets, the cooling tube being coupled to the water tank and the cooling sheets are coupled to the cooling tube;
   a water pump comprising a stirring fan and a drive motor, wherein the stirring fan is accommodated in the accommodating space to drive the electrolyzed water flowing, and the drive motor is configured for driving the stirring fan to promote the electrolyzed water flowing to cooling tube; and
   an output tube configured in the accommodating space of the water tank to receive the electrolyzed water driven by the stirring fan, wherein the cooling tube comprises a first port and a second port communicating with the accommodating space, and the first port faces the output tube to receive the electrolyzed water from the output tube.

2. The gas generating apparatus of claim 1, further comprising a delivery device disposed in the accommodating space of the water tank, wherein the stirring fan is configured in the delivery device, and the output tube is coupled to the delivery device.

3. The gas generating apparatus of claim 1, wherein a surface of the cooling tube has a copper powder sintered layer.

4. The gas generating apparatus of claim 1, further comprising a heat pipe, wherein an endothermic end of the heat pipe is configured on the cooling device.

5. The gas generating apparatus of claim 4, wherein the endothermic end of the heat pipe has a flat structure; the flat structure has a recession, and the cooling device is coupled to the recession.

6. The gas generating apparatus of claim 1, wherein the drive motor has a shell, and the shell has no control circuit board inside; the gas generating apparatus further comprises a control circuit board configured outside the shell and electrically connected to the drive motor, and the control circuit board is configured for controlling the drive motor to drive the stirring fan.

7. The gas generating apparatus of claim 2, wherein the delivery device has a preformed pore, the water pump further comprises a seal ring, and the drive motor is coupled to the hole by the seal ring.

8. The gas generating apparatus of claim 1, wherein the drive motor drives the stirring fan by magnetic coupling.

9. The gas generating apparatus of claim 1, wherein the stirring fan is suspended in the electrolyzed water.

10. The gas generating apparatus of claim 2, further comprising a connecting component, wherein the stirring fan is coupled to the delivery device by the connecting component.

11. A gas generating apparatus, comprising:
    a water tank comprising a casing and forming an accommodating space for accommodating an electrolyzed water and further having an outer surface;
    an electrolytic device disposed in the accommodating space of the water tank and configured for generating a hydrogen;
    a cooling device comprising at least one cooling tube and a plurality of cooling sheets, the cooling tube being coupled to the upper part of the water tank and the cooling sheets are coupled to the cooling tube; and
    a water pump comprising a stirring fan and a drive motor, wherein the stirring fan is accommodated in accommodating space to promote the electrolyzed water flowing through the cooling device, and the drive motor is configured for driving the stirring fan to promote the electrolyzed water flowing;
    wherein, the bottom part of the casing of the water tank forms a hollow space to contain the drive motor.

12. The gas generating apparatus of claim 11, wherein the drive motor has a shell, and the shell has no control circuit board inside; the gas generating apparatus further comprises a control circuit board configured outside the shell and electrically connected to the drive motor, and the control circuit board is configured for controlling the drive motor to drive the stirring fan.

13. The gas generating apparatus of claim 11, wherein the cooling device further comprises a cooling tube, and a surface of the cooling tube has a copper powder sintered layer.

14. The gas generating apparatus of claim 11, further comprising a heat pipe, wherein an endothermic end of the heat pipe is configured on the cooling device.

15. The gas generating apparatus of claim 14, wherein the endothermic end of the heat pipe is formed by partial housing of the cooling device.

16. The gas generating apparatus of claim 14, wherein the endothermic end of the heat pipe has a flat structure; the flat structure has a recession, and the cooling device is coupled to the recession.

17. The gas generating apparatus of claim 11, wherein the water pump further comprises a fixing component configured for fixing the drive motor on the casing.

18. The gas generating apparatus of claim 11, wherein the drive motor is a DC brushless motor.

19. The gas generating apparatus of claim 11, further comprising a delivery device disposed in the accommodating space of the water tank, wherein the stirring fan is configured in the delivery device; the gas generating apparatus further comprises an output tube disposed in the accommodating space of the water tank to receive and output the electrolyzed water from the delivery device; the cooling tube comprises a first port and a second port communicating with the accommodating space, the first port faces the output tube to receive the electrolyzed water from the output tube and the second port is configured to output the electrolyzed water flowing through the cooling tube.

* * * * *